United States Patent [19]

Sauerberg et al.

[11] Patent Number: 5,043,345

[45] Date of Patent: Aug. 27, 1991

[54] PIPERIDINE COMPOUNDS AND THEIR PREPARATION AND USE

[75] Inventors: Per Sauerberg, Valby; Preben H. Olesen, Copenhagen, both of Denmark

[73] Assignee: Novo Nordisk A/S, Bagsvaerd, Denmark

[21] Appl. No.: 401,370

[22] Filed: Aug. 31, 1989

[30] Foreign Application Priority Data

Feb. 22, 1989 [DK] Denmark .............................. 0825/89
May 12, 1989 [DK] Denmark .............................. 2315/89

[51] Int. Cl.⁵ .................... C07D 417/04; A61K 31/44
[52] U.S. Cl. .................................... 514/342; 514/340; 546/277
[58] Field of Search ................ 546/277, 276; 514/340, 514/342

[56] References Cited

U.S. PATENT DOCUMENTS 4,952,587  8/1990  Baker et al. ........................ 514/305

FOREIGN PATENT DOCUMENTS 154287  9/1987  Denmark .
307142  3/1989  European Pat. Off. .

*Primary Examiner*—Jane T. Fan
*Attorney, Agent, or Firm*—Steve T. Zelson

[57] ABSTRACT

The present invention relates to therapeutically active piperidine compounds, a method of preparing the same and to pharmaceutical compositions comprising the compounds. The novel compounds are useful as stimulants of the cognitive function of the forebrain and hippocampus of mammals and especially in the treatment of Alzheimer's disease.

8 Claims, No Drawings

PIPERIDINE COMPOUNDS AND THEIR PREPARATION AND USE

TABLE OF CONTENTS

Abstract of the Disclosure
2.0—Background of the Invention
3.0—Summary of the Invention
4.0—Detailed Description of the Invention
  4.1—Preparation and Characteristics of The Active Compounds
  4.2—Pharmacological and Other Properties of the Active Compounds
  4.3—Pharmaceutical Compositions Containing the Active Compounds
  4.4—Methods of Treatment Using the Active Compounds
5.0—Examples
  5.1—Example 1
    5.1. A—3-(4-chloro-1,2,5-thiadiazol-3-yl pyridine
    5.1. B—3-(4-methoxy-1,2,5-thiadiazol-3-yl) pyridine
    5.1. C—3-(4-methoxy-1,2,5-thiadiazol-3-yl) -1-methyl-pyridinium iodide
    5.1. D—1,2,5,6-tetrahydro-3-(4-methoxy-1,2, 5-thiadiazol-3-yl)-1-methylpyridine oxalate
  5.2—Example 2
    5.2. A—3-(4-ethoxy-1,2,5-thiadiazol-3-yl) pyridine
    5.2. B—3-(4-ethoxy-1,2,5-thiadiazol-3-yl) -1-methyl-pyridinium iodide
    5.2. C—3-(4-ethoxy-1,2,5-thiadiazol-3-yl) -1,2,5,6-tetrahydro-1-methylpyridine oxalate
  5.3—Example 3
    5.3. A—3-(4-propoxy-1,2,5-thiadiazol-3-yl) pyridine
    5.3. B—3-(4-propoxy-1,2,5-thiadiazol-3-yl)-1-methylpyridinium iodide
    5.3. C—1,2,5,6-tetrahydro-1-methyl-3-(4-propoxy-1,2,5-thiadiazol-3-yl)pyridine oxalate
  5.4 Example 4
    5.4 A—3-(4-butoxy-1,2,5-thiadiazol-3-yl) pyridine
    5.4. B—3-(4-butoxy-1,2,5-thiadiazol-3-yl)-1-methylpyridinium iodide
    5.4. C—3-(4-butoxy-1,2,5-thiadiazol-3-yl) -1,2,5,6-tetrahydro-1-methylpyridine oxalate
  5.5 Example 5
    5.5. A—3-(4-isopropoxy-1,2,5-thiadiazol-3-yl) pyridine
    5.5. B—3-(4-isopropoxy-1,2,5-thiadiazol-3-yl) -1-methylpyridinium iodide
    5.5. C—1,2,5,6-tetrahydro-3-(4-isopropoxy-1,2,5,thiadiazol-3-yl)1-methylpyridine oxalate
  5.6 Example 6
    5.6. A—3-(4-pentyloxy-1,2,5-thiadiazol-3-yl) pyridine
    5.6. B—3-(4-pentyloxy-1,2,5-thiadiazol-3-yl) methylpyridinium iodide
    5.6. C—1,2,5,6-tetrahydro-1-methyl-3-(4-pentyloxyl, 2,5-thiadiazol-3-yl) pyridine oxalate
  5.7 Example 7
    5.7 A—3-(4-isobutoxy-1,2,5-thiadiazol-3-yl) pyridine
    5.7. B—3-(4-isobutoxy-1,2,5-thiadiazol-3-yl) -1-methylpyridinium iodide
    5.7. C—1,2,5,6-tetrahydro-3-(4-isobutoxy-1,2,5-thiadiazol-3-yl)-1-methylpyridine oxalate
  5.8 Example 8
    5.8. A—3-(4-isopentyloxy-1,2,5-thiadiazol-3-yl) pyridine
    5.8. B—3-(4-isopentyloxy-1,2,5-thiadizaol-3-yl) -1-methylpyridinium iodide
    5.8. C—1,2,5,6-tetrahydro-3-(-4-isopentyloxy-1,2,5-thiadiazol-3-yl)-1-methylpyridine oxalate
  5.9 Example 9
    5.9. A—3-(4-hexyloxy-1,2,5-thiadiazol-3-yl) pyridine
    5.9. B—3-(4-hexyloxy-1,2,5-thiadiazol-3-yl)-1-methylpyridinium iodide
    5.9 C.—3-(4-hexyloxy-1,2,5-thiadiazol-3-yl) -1,2,5,6-tetrahydro-1-methylpyridine oxalate
  5.10 Example 10
    5.10. A—3-(4-benzyloxy-1,2,5-thiadiazol-3-yl) pyridine
    5.10. B—3-(4-benzyloxy-1,2,5-thiadiazol-3-yl) -1-methylpyridinium iodide
    5.10. C—3-(4-benzyloxy-1,2,5-thiadiazol-3-yl)-1,2,5,6-tetrahydro-1-methylpyridine oxalate
  5.11 Example 11
    5.11. A—3-(4-(3-butenyloxy-1,2,5-thiadiazol -3-yl)pyridine
    5.11. B—3-(4-(3-butenyloxy)-1,2,5-thiadiazol -3-yl)1-methylpyridinium iodide
    5.11. C—3-(4-(3-butenyloxy)-1,2,5-thiadiazol -3-yl)1,2,5,6-tetrahydro-1-methylpyridine oxalate
  5.12 Example 12
    5.12 A—3-(4-(2-butynyloxy-1,2,5-thiadiazol-3-yl) pyridine
    5.12. B—3-(4-(2-butynyloxy)-1,2,5-thiadiazol -3-yl)-1-methylpyridinium iodide
    5.12. C—3-(4-(2-butynyloxy)-1,2,5-thiadiazol -3-yl)-1,2,5,6-tetrahydro 1-methylpyridine oxalate
  5.13 Example 13
    5.13. A—3(4-propargyloxy-1,2,5-thiadiazol-3-yl) pyridine
    5.13. B—3-(4-propargyloxy-1,2,5-thiadiazol-3-yl) -1-methylpyridinium iodide
    5.13. C—1,2,5,6-tetrahydro-1-methyl-3-(4-propargyloxy-1,2,5-thiadiazol-3-yl) pyridine oxalate
  5.14 Example 14
    5.14. A—3-(4-cyclopropylmethoxy-1,2,5-thiadiazol -3-yl)pyridine
    5.14. B—3-(4-cyclopropylmethoxy-1,2,5-thiadiazol -3-yl)-1-methylpyridinium iodide
    5.14. C—3-(4-cyclopropylmethoxy-1,2,5-thiadiazol -3-yl)-1,2,5,6-tetrahydro-1-methylpyridine oxalate
  5.15 Example 15
    5.15. A—3-(4-chloro-1,2,5-thiadiazol-3yl)-1-methylpyridinium iodide
    5.15. B—3-(4-chloro-1,2,5-thiadiazol-3-yl)-1,2,5,6tetrahydro-1-methylpyridine oxalate
    5.15. C—1,2,5,6-tetrahydro-3-(4-methoxyethoxy -1,2,5-thiadiazol-3-yl)-1-methylpyridine oxalate
    5.15. D—3-(4-chloro-1,2,5-thiadiazol-3-yl) -1,2,5,6-tetrahydropyridine hydrochloride
    5.15. E—3-(4-butoxy-1,2,5-thiadiazol-3-yl) -1,2,5,6-tetrahydropyridine oxalate
  5.16 Example 16
    5.16. A—3-(4-chloro-1,2,5-thiadiazol-3-yl)-1-ethyl-pyridinium iodide
    5.16. B—3-(4-chloro-1,2,5,6-thiadiazol-3-yl) -1-ethyl-1,2,5,6-tetrahydropyridine oxalate
  5.17 Example 17
    5.17. A—3-(4-ethoxy-1,2,5-thiadiazol-3-yl)-1-ethyl-pyridinium iodide 5.17. B—3-(4-ethoxy-1,2,5,6-thiadiazol-3-yl)-1-ethyl-1,2,5,6-tetrahydropyridine oxalate 5.18 Example 18

5.18 A—Hydroxyimino-3-pyridylacetonitrile 5.18 B—Hydroxyimino-3-pyridyl-methylamidoxime 5.18 C—3-(3-amino-1,2,5-oxadiazol-4-yl) pyridine 5.18 D—3-(3-Amino-1,2,5-oxadiazol-4-yl) -1-methylpyridinium iodide 5.18 E—3-(3-Amino-1,2,5-oxadiazol-4-yl)-1,2,5,6-tetrahydro-1-methylpyridineoxalate

CLAIMS

2.0 BACKGROUND OF THE INVENTION

Due to the in general improved health situation in the western world, elderly-related diseases are much more common now than in the past and are likely to be even more common in the future.

One of the elderly-related symptoms is a reduction of the cognitive functions. This symptom is especially pronounced in the pathophysiological disease known as Alzheimer's disease. The disease is combined with, and also most likely caused by, a up to 90% degeneration of the muscarinic cholinergic neurons in nucleus basalis, which is part of substantia innominata. These neurons project to the prefrontal cortex and hippocampus and have a general stimulatory effect on the cognitive functions of the forebrain as well as of hippocampus, namely learning, association, consolidation, and recognition.

It is a characteristic of Alzheimer's disease that although the cholinergic neurons degenerate, the postsynaptic muscarinic receptors in the forebrain and hippocampus still exist. Therefore, muscarinic cholinergic agonists are useful in the treatment of Alzheimer's disease and in improving the cognitive functions of elderly people.

It is well known that arecoline (methyl 1-methyl-1,2,5,6-tetrahydropyridine-3-carboxylate) is such a cholinergic agonist (See Formula A)

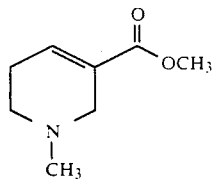

(A)

Arecoline, however, has a very short biological half life and a small separation between central and peripheral muscarinic effects. Furthermore, arecoline is a rather toxic compound. It is also known that 3-acetoxyquinuclidine is a muscarinic agonist (See Formula B)

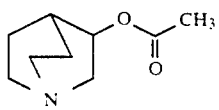

(B)

However, the disadvantage of this compound are the same as indicated for arecoline.

It is, therefore, an object of the present invention to provide new muscarinic cholinergic compounds having different structures and different levels of activity.

3.0 SUMMARY OF THE INVENTION

The novel compounds of the invention are of formula I:

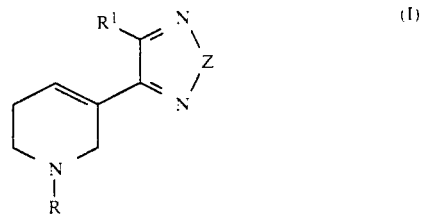

(I)

wherein Z is oxygen or sulphur, R is H, $C_{1-3}$-alkyl, $C_{3-4}$-cycloalkyl, $C_{2-4}$-alkenyl or $C_{2-4}$-alkynyl and $R^1$ is $C_{1-10}$-alkyl, $C_{2-10}$-alkenyl, $C_{2-10}$-alkynyl, $C_{3-7}$-cycloalkyl, $C_{1-10}$-alkoxy, benzyloxy, $C_{1-10}$-alkylthio, halogen, amino, $C_{1-10}$-alkylamino, $C_{2-10}$-dialkylamino or $C_{1-10}$-alkoxyamino or a salt thereof with a pharmaceutically-acceptable acid.

Examples of such salts include inorganic and organic acid addition salts such as hydrocholoride, hydrobromide, sulphate, phosphate, acetate, fumarate, maleate, citrate, lactate, tartrate, oxalate, or similar pharmaceutically-acceptable inorganic and organic acid addition salts.

This invention also includes a method for producing compounds of formula I with alkylation and reduction reactions of the appropriate pyridine compounds. In addition, the invention herein further comprises pharmaceutically compositions incorporating the compounds of formula I along with methods for treating Alzheimer's disease with these compounds.

4.0 DETAILED DESCRIPTION OF THE INVENTION

4.1 Preparation and Characteristics of the Active Compounds

The invention comprises a method of preparing 3-(1,2,5-oxadiazol-3-yl)or3-(1,2,5-thiadiazol-3-yl)-1,2,5,6-tetrahydropyridine compounds having the general formula I:

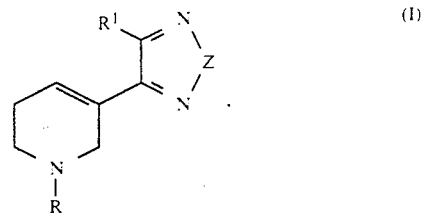

(I)

by alkylating a compound having the formula II

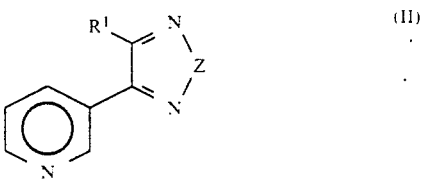

(II)

with an alkyl halide and reducing the compound thus formed with hydride ions to form a compound having the formula I wherein R is H, $C_{1-3}$-alkyl, $C_{3-4}$-cycloalkyl, $C_{2-4}$-alkenyl or $C_{2-4}$-alkynyl and $R^1$ is $C_{1-10}$-alkyl, $C_{2-10}$-alkenyl, $C_{2-10}$-alkynyl, $C_{3-7}$-cycloalkyl, $C_{1-10}$-alkoxy, phenoxy, benzyloxy, $C_{1-10}$-alkylthio, halogen, amino, $C_{1-10}$-alkylamino, $C_{2-10}$-dialkylamino or $C_{1-10}$-alkoxyamino and a salt therefore with a pharmaceutically-acceptable acid.

All of the below shown structures are known to have affinity for the muscarinic receptors, but only the 3-alkyl-1,2,4-oxadiazol-5-yls (III and VII) and the 3-alkyl-1,2,4-thiadiazol-5-yls (IV and VIII) are agonists. The 5-alkyl-1,2,4-oxadiazol-3-yls (V and IX) and the 5-alkyl-1,2,4-thiadiazol-3-yls (VI and X) are antagonists.

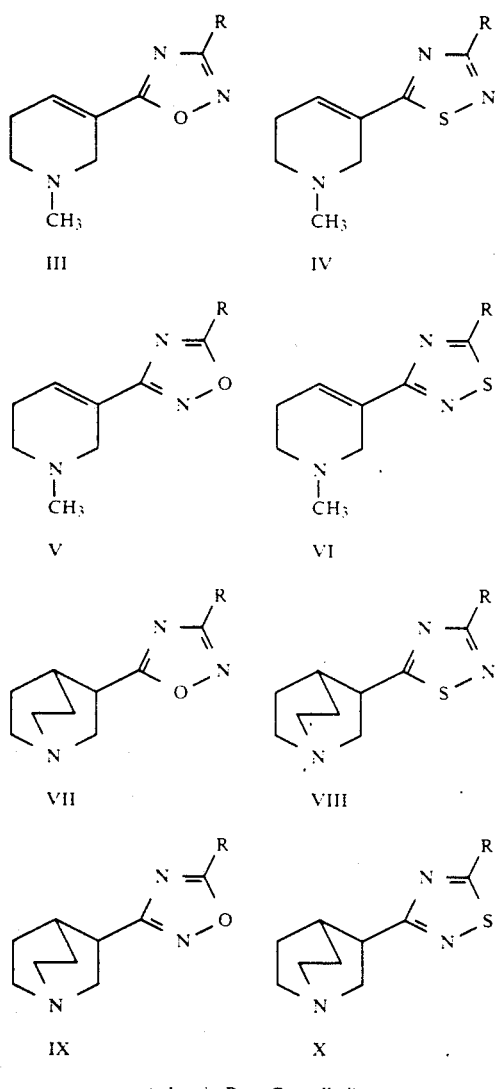

(wherein R = $C_{1-2}$ alkyl)

A common feature for all of the shown heterocycles with affinity for muscarinic receptors is that the substituent (R) always is in the beta position relative to the cyclic amine:

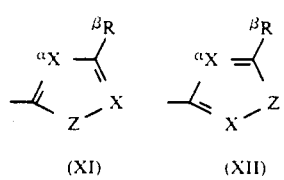

-continued
X = C or N
Z = O or S

The difference between XI and XII is in the electronic distribution in the heterocycle. In other words, in XI the double bonds are in another relative position to the substituent than in XII.

Without wishing to be bound by any theory or mechanism it is believed that this is probably why structures with the general structure XI are muscarinic agonists and structures with the general structure XII are muscarinic antagonists.

It is therefore very surprising that heterocycles with a substitutent in the alpha position to the cyclic amine as with the active compounds disclosed and claimed herein are extremely effective ester isosters. There are no known alpha-substituted heterocycles being ester isosteres.

For instance,3-(3-subst.-1,2,5-thiadiazol-4-yl)-1,2,5,6-tetrahydro-1-methylpyridines (XIII) have been found to be very potent muscarinic agonists with a better $M_1$-selectively than agonists with the substituent in the beta position.

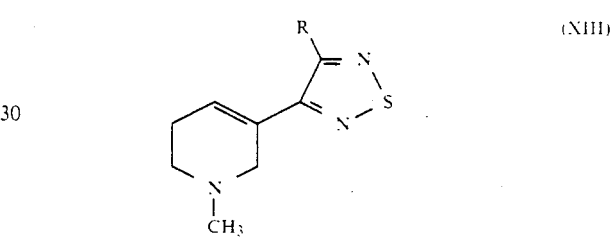

Furthermore, not all alpha-substituted heterocycles are ester isosters. It is believed that the position of the double bonds relative to the substituent (R) is very important. If the electrostatic properties are different from the one indicated in the heterocycle of structure XIII, the muscarinic agonist activity decrease dramatically. Compounds with the general formula XIV are either antagonists or inactive

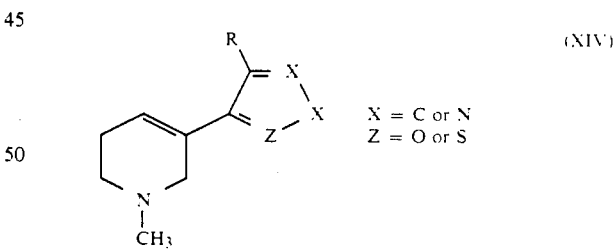

The heterocycles with the general formula XV are, therefore, both structurally and biologically different from the general structures XI, XII and XIV.

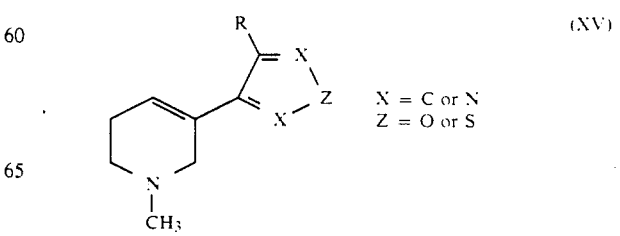

That the compounds XIII fit the muscarinic receptors better than the structures III to X is reflected in the fact that the substituent (R) is allowed to be bigger and more lipophilic without losing affinity and agonist activity. In fact, it is the C4-8-alkoxy that show the best $M_1$-selectivity.

4.2 Pharmacological and Other Properties of the Active Compounds

The pharmacological properties of the compounds of the present invention (Formula I) can be illustrated by determining their capability to inhibit the specific binding of $^3$H-Oxotremorine-M ($^3$H—Oxo)

$^3$H—Oxo labels muscarinic receptors in the CNS (with a preference for agonist domaines of the receptors). Three different sites are labelled by $^3$H—Oxo. These sites have affinity of 1.8, 20 and 3000 nM, respectively. Using the present experimental conditions only the high and medium affinity sites are determined. The inhibitory effects of compounds on $^3$H-Oxo binding reflects the affinity for muscarinic acetylcholine receptors.

All preparations are performed at 0°-4° C. unless otherwise indicated. Fresh cortex (0.1-1 g) from male Wistar rats (150-250 g) is homogenized for 5-10 s in 10 ml 20 mM Hepes pH: 7.4, with an Ultra-Turrax homogenizer. The homogenizer is rinsed with 10 ml of buffer and the combined suspension centrifuged for 15 min at 40,000× g. The pellet is washed three times with buffer. In each step the pellet is homogenized as before in 2×10 ml of buffer and centrifuged for 10 min at 40,000×g. The final pellet is homogenized in 20 mM Hepes pH: 7.4 (100 ml per g or original tissue) and used for binding assay. Aliquots of 0.5 ml is added 25 ul of test solution and 25 ul of 3H-Oxotremorine (1.0 nM, final concentration) mixed and incubated for 30 min at 25° C. Non-specific binding is determined in triplicate using Arecolin (1 ug/ml, final concentration) as the test substance. After incubation samples are added 5 ml of ice-cold buffer and poured directly onto Whatman GF/C glass fiber filters under suction and immediately washed 2 times with 5 ml of ice-cold buffer. The amount of radioactivity on the filters are determined by conventional liquid scintillation counting. Specific binding is total binding minus non-specific binding. Test substances are dissolved in 10 ml water (if necessary heated on a steambath for less than 5 minutes) at a concentration of 2.2 mg/ml. 25-75% inhibition of specific binding must be obtained before calculation of $IC_{50}$.

The test value will be given as $IC_{50}$ (the concentration (ng/ml) of the test substance which inhibits the specific binding of $^3$H-Oxo by 50%).

$$IC_{50} = \text{(applied test substance concentration)} \times \frac{1}{\left(\frac{C_o}{C_x} - 1\right)} \text{ng/ml}$$

where $C_o$ is specific binding in control assays and $C_x$ is the specific binding in the test assay. (The calculations assume normal mass-action kinetics).

Test results obtained by testing some compounds of the present invention will appear from the following Table 1.

TABLE 1

| Compound No. | Inhibition in vitro OXO BINDING (ng/ml) |
|---|---|
| 1 | 1.5 |
| 2 | 0.4 |
| 3 | 0.2 |
| 4 | 0.5 |
| 5 | 3.5 |
| 6 | 1.9 |
| 7 | 1.7 |
| 8 | 1.9 |
| 9 | 3.6 |
| 10 | 2.3 |
| 11 | 0.9 |
| 12 | 0.3 |
| 13 | 0.3 |
| 14 | 0.4 |
| 15 | 3.6 |
| 16 | 3.3 |
| 17 | 19.0 |
| 18 | 3.6 |
| 19 | 92 |
| 20 | 5.9 |

4.3 Pharmaceutical Compositions Containing the Active Compounds

The compounds of the present invention, together with a conventional adjuvant, carrier, or diluent, and if desired in the form of a pharmaceutically-acceptable acid addition salt thereof, may be placed in the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective muscarinic cholinergic agonistic amount of the active ingredient commensurate with the intended daily dosage range to be employed. Tablets containing ten (10) milligrams of the active ingredient or, more broadly, one (1) to hundred (100) milligrams, per tablet, are accordingly suitable representative unit dosage forms.

The compounds of this invention can thus be used for the formulation of pharmaceutical preparations, e.g. for oral and parenteral administration to mammals including humans, in accordance with conventional methods of galenic pharmacy.

Conventional excipients are such pharmaceutically acceptable organic or inorganic carrier substances suitable for parenteral or enteral application which do not deleteriously react with the active compounds.

Examples of such carriers are water, salt solutions, alcohols, polyethylene glycols, polyhydroxyethoxylated castor oil, gelatine, lactose, amylase, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated caster oil.

Ampoules are convenient unit dosage forms.

Tablets, dragees, or capsules having talc and/or a carbohydrate carrier or binder or the like, the carrier preferably being lactose and/or corn starch and/or potato starch, are particularly suitable for oral application. A syrup, elixir of the like can be used in cases where a sweetened vehicle can be employed.

Generally, the compounds of this invention are dispensed in unit form comprising 1-100 mg in a pharmaceutically acceptable carrier per unit dosage.

The dosage of the compounds according to this invention is 1-100 mg/day, preferably 10-70 mg/day, when administered to patients, e.g. humans, as a drug.

A typical tablet which may be prepared by conventional tabletting techniques contains:

| Active Compound | 5.0 mg |
|---|---|
| Lactosum | 67.8 mg Ph. Eur. |
| Avicel ® | 31.4 mg |
| Amberlite ® | 1.0 |
| Magnesii stearas | 0.25 mg. Ph. Eur. |

4.4 Methods of Treatment using the Active Compounds

Due to the high muscarinic cholinergic receptor agonistic activity, the compounds of the invention are extremely useful in the treatment symptoms related to a reduction of the cognitive functions of the brain of mammals, when administered in an amount effective for stimulating the cognitive functions of the forebrain and hippocampus. The important stimulating activity of the compounds of the invention includes both activity against the pathophysiological disease, Alzheimer's disease, as well as against normal degeneration of brain function.

The compounds of the invention may accordingly be administered to a subject, e.g., a living animal body, including a human, in need of stimulation of the cognitive functions of the forebrain and hippocampus, and if desired in the form of a pharmaceutically-acceptable acid addition salt thereof (such as hydrobromide, hydrochloride, or sulfate, in any event prepared in the usual or conventional manner, e.g., evaporation to dryness of the free base in solution together with the acid), ordinarily concurrently, simultaneously, or together with a pharmaceutically-acceptable carrier or diluent, especially and preferably in the form of a pharmaceutical composition thereof, whereof by oral, rectal, or parenteral (including subcutaneous) route, in an effective forebrain and hippocampus stimulating amount, and in any event an amount which is effective for improving the cognitive function of mammals due to their muscarinic cholinergic receptor agonistic activity.

Suitable dosage ranges are 1-100 milligrams daily, 10-100 milligrams daily, and especially 30-70 milligrams daily, depending as usual upon the exact mode of administration, form in which administered, the indication toward which the administration is directed, the subject involved and the body weight of the subject involved, and the preference and experience of the physician or veterinarian in charge.

5.0 EXAMPLES

The preferred methods for the preparation of the active compounds of this invention are illustrated in the following examples in more detail.

5.1 Example 1

5.1.A 3-(4-chloro-1,2,5-thiadiazol-3-yl)pyridine

To a solution of sulfurmonochloride (2.4 ml, 30 mmol) in N,N-dimethylformamide (5 ml) was slowly added alphaaminoalphaaminoalpha(3-pyridyl)acetonitril (Archive der Pharmazie 289 (4) (1956)) (1.70 g, 10 mmol). The reaction mixture was stirred at room temperature for 18 h. Water (20 ml) was added and the aqueous phase was extracted with ether. The combined ether phases were dried and evaporated. The residue was purified by column chromatography (SiO$_2$, eluent: ethyl acetate/methylene chloride (1:1)). The title compound was collected in 45% (880 mg) yield. M+: 197.

5.1.B 3-(4-methoxy-1,2,5-thiadiazol-3-yl)pyridine

To a solution of sodium (460 mg, 20 mmol) in methanol (10 ml) was added 3-(4-chloro-1,2,5-thiadiazol-3-yl)pyridine (750 mg, 3.8 mmol). The mixture was stirred at 50° C. for 1 h and evaporated. The residue was dissolved in water and extracted with methylene chloride. The combined organic phases were dried and evaporated to give the title compound, which crystallized with petroleum ether in a yield 630 mg (86%).

5.1.C 3-(4-methoxy-1,2,5-thiadiazol-3-yl)-1-methyl-pyridinium iodide

A mixture of methyl iodide (0.37 ml, 6 mmol) and 3(4-methoxy-1,2,5-thiadiazol-3-yl)pyridine (500 mg, 2.5 mmol) in acetone (10 ml) was stirred at room temperature for 18 h. The title compound precipitated from the solution and was collected by filtration for a yield 1.0 g (100%).

5.1.D 1,2,5,6-tetrahydro-3-(4-methoxy-1,2,5-thiadiazol-3-yl)-1-methylpyridine oxalate Sodium borohydride (460 mg, 12 mmol) was added to a solution of 3-(4-methoxy-1,2,5-thiadiazol-3-yl)-1-methylpyridinium iodide (1.0 g, 3 mmol) in ethanol (99.9%, 20 ml) and the reaction mixture was stirred at room temperature for 1 h. After evaporation the residue was dissolved in water and extracted with methylene chloride. The dried organic phases were evaporated and the residue purified by column chromatography (SiO$_2$, eluent: ethyl acetate/methanol (4:1)). The title compound was crystallized as the oxalate salt from acetone for a yield 390 mg.(Mp 150° C.; M+211; Compound 1)

5.2 Example 2

5.2.A 3-(4-ethoxy-1,2,5-thiadiazol-3-yl)pyridine

To a solution of sodium (440 mg, 17 mmol) in ethanol (10 ml) was added 3-(4-chloro-1,2,5-thiadiazol-3-yl)pyridine (650 mg, 3.3 mmol). The mixture was stirred at 40° C. for 10 h and evaporated. The residue was dissolved in water and extracted with methylene chloride. The combined organic phases were dried and evaporated to yield 520 mg (76%) of the title compound.

5.2.B
3-(4-ethoxy-1,2,5-thiadiazol-3-yl)-1-methylpyridinium iodide

A mixture of methyl iodide (0.3 ml, 5 mmol) and 3-(4-ethoxy-1,2,5-thiadiazol-3-yl)pyridine (520 mg, 2.5 mmol) in acetone (10 ml) was stirred at room temperature for 18 h. The title compound precipitated from the solution and was collected by filtration to yield 0.72 g (83%).

5.2.C
3-(4-ethoxy-1,2,5-thiadiazol-3-yl)-1,2,5,6-tetrahydrolmethylpyridine oxalate.

Sodium borohydride (300 mg, 8 mmol) was added to a solution of 3-(4-ethoxy-1,2,5-thiadiazol-3-yl)-1-methylpyridinium iodide (0.72 g, 2 mmol) in ethanol (99.9%, 20 ml) and the reaction mixture was stirred at room temperature for 1 h. After evaporation the residue was dissolved in water and extracted with methylene chloride. The dried organic phases were evaporated and the residue purified by column chromatography (SiO$_2$, eluent: ethyl acetate/methanol (4:1)). The title compound was crystallized as the oxalate salt from acetone, and recrystallized from methanol to yield 190 mg (Mp 137° C.; M+225; Compound 2).

5.3 Example 3

5.3.A 3-(4-propoxy-1,2,5-thiadiazol-3-yl)pyridine

To a solution of sodium (440 mg, 17 mmol) in 1-propanol (10 ml) was added 3-(4-chloro-1,2,5-thiadiazol-3-yl)pyridine (650 mg, 3,3 mmol). The mixture was stirred at 50° C. for 2 h and evaporated. The residue was dissolved in water and extracted with methylene chloride. The combined organic phases were dried and evaporated to yield 700 mg (96%) of the title compound.

5.3.B
3-(4-propoxy-1,2,5-thiadiazol-3-yl)-1-methylpyridinium iodide.

A mixture of methyl iodide (0.37 ml, 6 mmol) and 3-(4-propoxy-1,2,5-thiadiazol-3-yl)pyridine (700 mg, 3.1 mmol) in acetone (10 ml) was stirred at room temperature for 18 h. The title compound precipitated from the solution and was collected by filtration to yield 0.98 g (88%).

5.3.C 1,2,5,6-tetrahydro-1-methyl-3-(4-propoxy -1,2,5-thiadiazol-3-yl)pyridine oxalate Sodium borohydride 380 mg, 10 mmol) was added to a solution of 3-(4-propoxy-1,2,5-thiadiazol- 3-yl)-1 methylpyridinium iodide (980 mg, 2.7 mmol) in ethanol (99.9%, 20 ml) and the reaction mixture was stirred at 0° C. for 1 h. After evaporation the residue was dissolved in water and extracted with ethyl acetate. The dried organic phases were evaporated and the residue purified by column chromatography (SiO$_2$ eluent: ethyl acetate/methanol (4:1)). The title compound was crystallized as the oxalate salt from acetone to yield 440 mg (Mp 148° C.; M+: 239; Compound 3).

5.4 Example 4

5.4.A 3-(4-butoxy-1,2,5-thiadiazol-3-yl)pyridine

To a solution of sodium (290 mg, 12.5 mmol) in n-butanol (10 ml) was added 3-(4-chloro-1,2,5-thiadiazol-3-yl)pyridine (490 mg, 2.5 mmol). The mixture was stirred at 25° C. for 18 h and evaporated. The residue was dissolved in water and extracted with methylene chloride. The combined organic phases were dried and evaporated to yield 580 mg (100%) of the title compound.

5.4.B
3-(4-butoxy-1,2,5-thiadiazol-3-yl)-1-methylpyridinium iodide

A mixture of methyl iodide (0.3 ml, 5 mmol) and 3(4-butoxy-1,2,5-thiadiazol-3-yl)pyridine (580 mg, 2.5 mmol) in acetone (5 ml) was stirred at room temperature for 18 h. The title compound precipitated from the solution and was collected by filtration to yield 0.60 g (64%).

5.4.C
3-(4-butoxy-1,2,5-thiadiazol-3-yl)-1,2,5,6-tetrahydro-1-methylpyridine oxalate Sodium borohydride (240 mg, 6.4 mmol) was added to a solution of 3-(4-butoxy-1,2,5-thiadiazol-3-yl)-1-methylpyridinium iodide (0.60 g, 1.6 mmol) in ethanol (99.9%, 20 ml) and the reaction mixture was stirred at 0° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 280 mg (Mp 158° C.; M−: 253; Compound 4).

5.5 Example 5

5.5.A 3-(4-isopropoxy-1,2,5-thiadiazol-3-yl)pyridine

To a solution of sodium (290 mg, 12.5 mmol) in isopropanol (10 ml) was added 3-(4-chloro-1,2,5-thiadiazol-3-yl)pyridine (490 mg, 2.5 mmol). The mixture was stirred at 25° C. for 18 h and evaporated. The residue was dissolved in water and extracted with ethyl acetate. The combined organic phases were dried and evaporated to yield 540 mg (98%) of the title compound.

5.5.B
3-(4-isopropoxy-1,2,5-thiadiazol-3-yl)-1-methyl-pyridinium iodide

A mixture of methyl iodide (0.3 ml, 5 mmol) and 3(4-isopropoxy-1,2,5-thiadiazol-3-yl)pyridine (540 mg, 2.4 mmol) in acetone (5 ml) was stirred at room temperature for 18 h. The title compound precipitated from the solution and was collected by filtration to yield 0.68 g (77%).

5.5.C 1,2,5,6-tetrahydra-3-(4-isopropoxy-1,2,5, thiadiazol- 3-yl)-1-methylpyridine oxalate Sodium borohydride (270 mg, 7.2 mmol) was added to a solution of 3-(4-isopropoxy-1,2,5-thiadiazol-3-yl)-1methylpyridinium iodide (650 mg, 1.8 mmol) in ethanol (99.9%, 20 ml) and the reaction mixture was stirred at 0° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 280 mg, (Mp 164° C.;. M−: 239; Compound 5).

5.6A 3-Example 6

5.6.A 3-(4-pentyloxy-1,2,5-thiadiazol-3-yl)pyridine

To a solution of sodium (230 mg, 10 mmol) in 1-pentanol (20 ml) was added 3-(4-chloro-1,2,5-thiadiazol 3-yl)pyridine (490 mg, 2.5 mmol). The mixture was stirred at 50° C. for 3 h and evaporated. The residue was dissolved in water and extracted with methylene chloride. The combined organic phases were dried and evaporated to give the wanted compound.

5.6.B 3-(4-pentyloxy-1,2,5-thiadiazol-3-yl)-1-methylpyridinium iodide

A mixture of methyl iodide (0.3 ml, 5 mmol) and 3(4-pentyloxy-1,2,5-thiadiazol-3-yl)pyridine (620 mg, 2.5 mmol) in acetone (5 ml) was stirred at room temperature for 18 h. The title compound precipitated from the solution and was collected by filtration to yield 0.81 g (84%).

5.6.C 1,2,5,6-tetrahydro-1-methyl-3-(4-pentyloxy-1,2,5-thiadiazol-3-yl)pyridine oxalate Sodium borohydride (300 mg, 8 mmol) was added to a solution of 3-(4-pentyloxy-1,2,5-thiadiazol- 3-yl)-1-methylpyridinium iodide (0.81g, 2 mmol) in ethanol (99.9%, 20 ml) and the reaction mixture was stirred a 0° C. for 1 h. After evaporation the residue was dissolved in water and extracted with ether. The dried organic phases were evaporated and the residue purified by column chromatography (SiO$_2$, eluent: ethyl acetate/methanol (4:1)). The title compound was crystallized as the oxalate salt from acetone, and recrystallized from methanol to yield 220 mg (Mp 150° C.; M$^-$: 267; Compound 6).

5.7 Example 7

5.7.A 3-(4-isobutoxy-1,2,5-thiadiazol-3-yl)pyridine

To a solution of sodium (230 mg, 10 mmol) in isobutanol (20 ml) was added 3-(4-chloro-1,2,5-thiadiazol-3-yl)pyridine (490 mg, 2.5 mmol). The mixture was stirred at 50° C. for 3 h and evaporated. The residue was dissolved in water and extracted with methylene chloride. The combined organic phases were dried and evaporated to give the wanted compound.

5.7.B 3-(4-isobutoxy-1,2,5-thiadiazol-3-yl)-1-methylpyridinium iodide

A mixture of methyl iodide (0.6 ml, 10 mmol) and 3(4-isobutoxy-1,2,5-thiadiazol-3-yl)pyridine (588 mg, 2.5 mmol) in acetone (5 ml) was stirred at room temperature for 18 h. The title compound precipitated from the solution and was collected by filtration to yield 0.88 g (87%).

5.7.C 1,2,5,6-tetrahydro-3-(4-isobutoxy-1,2,5-thiadiazol-3-yl)-1-methylpyridine oxalate Sodium borohydride (160 mg, 4.3 mmol) was added to a solution of 3-(4-isobutoxy-1,2,5-thiadiazol- 3-yl)-1-methylpyridinium iodide (0.82 g, 2.2 mmol) in ethanol (99.9%, 20 ml) and the reaction mixture was stirred at 0° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 400 mg (Mp 135° C.; M$^+$: 253; Compound 7).

5.8 Example 8

5.8.A.3-(4-isopentyloxy-1,2,5-thiadiazol-3-yl)pyridine

To a solution of sodium (230 mg, 10 mmol) in isopentanol (20 ml) was added 3-(4-chloro-1,2,5-thiadiazol-3-yl)pyridine (490 mg, 2.5 mmol). The mixture was stirred at 50° C. for 2 h and evaporated. The residue was dissolved in water and extracted with ether. The combined organic phases were dried and evaporated to give the wanted compound.

5.8 B. 3-(4-isopentyloxy-1,2,5-thiadiazol-3-yl)-1-methylpyridinium iodide

A mixture of methyl iodide (0.5 ml, 10 mmol) and 3(4-isopentyloxy-1,2,5-thiadiazol-3-yl)pyridine (622 mg, 2.5 mmol) in acetone (5 ml) was stirred at room temperature for 18 h. The title compound precipitated from the solution and was collected by filtration to yield 0.78 g (81%).

5.8 C. 1,2,5,6-tetrahydro-3-(4-isopentyloxy-1,2,5-thiadiazol-3-yl)-1-methylpyridine oxalate Sodium borohydride (150 mg, 4 mmol) was added to a solution of 3-(4-isopentyloxy-1,2,5-thiadiazol- 3-yl)-1-methylpyridinium iodide (780 g, 2 mmol) in ethanol (99.9%, 20 ml) and the reaction mixture was stirred at 0° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 350 mg (Mp 152° C.; M$^-$: 267; Compound 8).

5.9 Example 9

5.9.A 3-(4-hexyloxy-1,2,5-thiadiazol-3-yl)pyridine

To a solution of sodium (230 mg, 10 mmol) in 1-hexanol (15 ml) was added3-(4-chloro-1,2,5-thiadiazol-3-yl)pyridine (490 mg, 2.5 mmol). The mixture was stirred at 50° C. for 2 h and evaporated. The residue was dissolved in water and extracted with ether. The combined organic phases were dried and evaporated to give the wanted compound.

5.9 B. 3-(4-hexyloxy-1,2,5-thiadiazol-3-yl)-1-methylpyridinium iodide

A mixture of methyl iodide (0.5 ml, 7.5 mmol) and 3-(4-hexyloxy-1,2,5-thiadiazol-3-yl)pyridine (658 mg, 2.5 mmol) in acetone (5 ml) was stirred at room temperature for 18h. The title compound precipitated from the solution and was collected by filtration to yield 0.81 g (80%).

5.9 C. 3-(4-hexyloxy-1,2,5-thiadiazol-3-yl)-1,2,5,6-tetrahydro-1-methylpyridine oxalate Sodium borohydride (230 mg, 6 mmol) was added to a solution of 3-(4-hexyloxy-1,2,5-thiadiazol-3-yl)-1-methylpyridinium iodide (810 mg, 2 mmol) in ethanol (99.9%, 20 ml) and the reaction mixture was stirred at room temperature for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 350 mg (Mp 148° C.; M+: 281; Compound 9).

5.10 Example 10

5.10 A. 3-(4-benzyloxy-1,2,5-thiadiazol-3-yl)pyridine

To a solution of sodium (490 mg, 2.5 mmol) in benzylalcohol (15 ml) was added 3-(4-chloro-1,2,5-thiadiazol-3-yl)pyridine (490 mg, 2.5 mmol). The mixture was stirred at 50° C. for 2 h and evaporated. The residue was dissolved in water and extracted with ether. The combined organic phases were dried and evaporated to give the wanted compound.

5.10 B.
3-(4-benzyloxy-1,2,5-thiadiazol-3-yl)-1-methylpyridinium iodide

A mixture of methyl iodide (0.5 ml, 7.5 mmol) and 3-(4-benzyloxy-1,2,5-thiadiazol-3-yl)pyridine (673 mg, 2.5 mmol) in acetone (5 ml) was stirred at room temperature for 18 h. The title compound precipitated from the solution and was collected by filtration to yield 0.75 g (73%).

5.10 C.
3-(4-benzyloxy-1,2,5-thiadiazol-3-yl)-1,2,5,6-tetrahydro-1-methylpyridine oxalate Sodium borohydride (230 mg, 6 mmol) was added to a solution of 3-(4-benzyloxy-1,2,5-thiadiazol-3-yl)1-methylpyridinium iodide (750 mg, 1.8 mmol) in ethanol (99.9%, 20 ml) and the reaction mixture was stirred at 0° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 340 mg (Mp 149° C.; M+: 287; Compound 10).

5.11 Example 11

5.11 A.
3-(4-(3-butenyloxy-1,2,5-thiadiazol-3-yl)pyridine

To a solution of 3-buten-1-ol (540 mg, 7.5 mmol) and sodiumhydride (180 mg, 7.5 mmol) in dry tetrahydrofuran was added a solution of 3-(4-chloro-1,2,5-thiadiazol 3-yl)-pyridine (490 mg, 2.5 mmol) in dry tetrahydrofuran. The reaction mixture was stirred at room temperature for 1 h. Water was added and the mixture was extracted with ether. The ether phase was dried and evaporated to yield 650 mg of the title compound.

5.11 B.
3-(4-(3-butenyloxy)-1,2,5-thiadiazol-3-yl)-1-methylpyridinium iodide A mixture of methyl iodide (0.5 ml, 7.5 mmol) and 3-(4-(3-butenyloxy)-1,2,5-thiadiazol-3-yl)pyridine (583 mg, 2.5 mmol) in acetone (5 ml) was stirred at room temperature for 18 h. The title compound precipitated from the solution and was collected by filtration to yield 890 g (96%).

5.11 C.
3-(4-(3-butenyloxy)-1,2,5-thiadiazol-3-yl)1,2,5,6-tetrahydro-1-methylpyridineoxalate Sodium borohydride (210 mg, 5.5 mmol) was added to a solution of 3-(4-(3-butenyloxy-1,2,5-thiadiazol 3-yl)-1-methylpyridinium iodide (1.03 g, 2.8 mmol) in ethanol (99.9%, 20 ml) and the reaction mixture was stirred at 0° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 380 mg (Mp 141° C.; M+: 251; Compound 11).

5.12 Example 12

5.12A. 3-(4-(2-butynyloxy-1,2,5-thiadiazol-3-yl)pyridine

To a solution of 2-butyn-1-ol (530 mg, 7.5 mmol) and sodiumhydride (180 mg, 7.5 mmol) in dry tetrahydrofuran was added a solution of 3-(4-chloro-1,2,5-thiadiazol-3-yl)-pyridine (490 mg, 2.5 mmol) in dry tetrahydrofuran. The reaction mixture was stirred at room temperature for 2 h. Water was added and the mixture was extracted with ether. The ether phase was dried and evaporated to give the title compound.

5.12 B.
3-(4-(2-butynyloxy)-1,2,5-thiadiazol-3-yl)-1-methylpyridinium iodide A mixture of methyl iodide (0.5 ml, 7.5 mmol) and 3-(4-(2-butynyloxy)-1,2,5-thiadiazol-3-yl)pyridine (578, mg, 2.5 mmol) in acetone (5 ml) was stirred at room temperature for 18 h. The title compound precipitated from the solution and was collected by filtration to yield 0.88 g (95%).

5.12 C.
3-(4-(2-butynyloxy)-1,2,5-thiadiazol-3-yl)-1,2,5,6-tetrahydro 1-methylpyridine oxalate Sodium borohydride (180 mg, 4.7 mmol) was added to a solution of 3-(4-(2-butynyloxy)-1,2,5-thiadiazol-3-yl)-1-methylpyridinium iodide (0.88 g, 2.35 mmol) in ethanol (99.9%, 20 ml) and the reaction mixture was stirred at 0° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone, and recrystallized in methanol to yield 140 mg (Mp 158° C.; M+: 249; Compound 12).

5.13 Example 13

5.13A. 3-(4-propargyloxy-1,2,5-thiadiazol-3-yl)pyridine

To a solution of propargylalcohol (420 mg, 7.5 mmol) and sodiumhydride (180 mg, 7.5 mmol) in dry tetrahydrofuran was added a solution of 3-(4-chloro-1,2,5-thiadiazolyl)-pyridine (490 mg, 2.5 mmol) in dry tetrahydrofuran. The reaction mixture was stirred at room temperature for 2 h. Water was added and the mixture was extracted with ether. The ether phase was dried and evaporated to yield 530 mg (98%) of the title compound.

5.13 B. 3-(4-propargyloxy-1,2,5-thiadiazol-3-yl)-1-methyl-pyridinium iodide

A mixture of methyl iodide (0.45 ml, 7.2 mmol) and 3-(4-propargyloxy-1,2,5-thiadiazol-3-yl)pyridine (430 mg, 2.4 mmol) in acetone (5 ml) was stirred at room temperature for 18 h. The title compound precipitated from the solution and was collected by filtration to yield 0.58 g (67%).

5.13 C. 1,2,5,6-tetrahydro-1-methyl-3-(4 propargyloxy1,2,5-thiadiazol-3-yl)pyridineoxalate Sodium borohydride (230 mg, 6 mmol) was added to a solution of 3-(4-propargyloxy-1,2,5-thiadiazol-3-yl)-1-methylpyridinium iodide (0.68 g, 1.9 mmol) in ethanol (99.9%, 20 ml) and the reaction mixture was stirred at 0° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 200 mg (Mp 155° C.; M$^+$: 235; Compound 13).

5.14 Example 14

5.14 A. 3-(4-cyclopropylmethoxy-1,2,5-thiadiazol-3-yl)pyridine

To a solution of cyclopropylcarbinol (360 mg, 5 mmol) and sodiumhydride (110 mg, 5 mmol) in dry tetrahydrofuran was added a solution of 3-(4-chloro-1,2,5-thiadiazol-3-yl)-pyridine (490 mg, 2.5 mmol) in dry tetrahydrofuran. The reaction mixture was stirred at room temperature for 3 h. Water was added and the mixture was extracted with ether. The ether phase was dried and evaporated to yield 400 mg (69%) of the title compound.

5.14B. 3-(4-cyclopropylmethoxy-1,2,5-thiadiazol-3-yl)1-methylpyridinium iodide A mixture of methyl iodide (0.25 ml, 4 mmol) and 3(4-cyclopropylmethoxy-1,2,5-thiadiazol-3-yl)pyridine(400 mg, 1.7 mmol) in acetone (5 ml) was stirred at room temperature for 36 h. The title compound precipitated from the solution and was collected by filtration to yield 0.41 g (65%).

5.14 C. 3-(4-cyclopropylmethoxy-1,2,5-thiadiazol-3yl) 1,2,5,6-tetrahydro-1-methylpyridine oxalate Sodium borohydride (170 mg, 4.4 mmol) was added to a solution of 3-(4-cyclopropylmethoxy-1,2,5-thiadiazol-3-yl)-1-methylpyridinium iodide (410 mg, 1.1 mmol) in ethanol (99.9%, 20 ml) and the reaction mixture was stirred at 0° C. for 1 h. After evaporation the residue was dissolved in water and extracted with ethyl acetate. The dried organic phases were evaporated and the residue purified by column chromatography (SiO$_2$, eluent: ethyl acetate/methanol (4:1)). The title compound was crystallized as the oxalate salt from acetone to yield 130 mg (Mp 153° C.; M$^+$: 251; Compound 14).

5.15 Example 15

5.15 A. 3-(4-chloro-1,2,5-thiadiazol-3-yl)-1-methylpyridinium iodide

A solution of 3-(4-chloro-1,2,5-thiadiazol-3-yl)pyridine (1.98 g, 10 mmol) and methyl iodide (4.25 g, 30 mmol) in acetone (10 ml) was stirred at room temperature for 16 h. The precipitate was collected by filtration to yield 3.40 g (100%) of the title compound.

5.15 B. 3-(4-chloro-1,2,5-thiadiazol-3-yl)-1,2,5,6 tetrahydro-1-methylpyridine oxalate To a suspension of sodium borohydride (330 mg, 8.6 mmol) in ethanol (20 ml) was added 3-(4-chloro-1,2,5-thiadiazol-3-yl)-1-methylpyridinium iodide (1.46 g, 4.3 mmol) at 0° C. The reaction mixture was stirred for 1 h at 0° C. Water was added and the mixture was extracted with ethyl acetate. After drying, the ethyl acetate phase was evaporated and the residue purified by column chromatography (eluent: ethyl acetate: methanol (4:1)).Yield 880 mg (95%). Crystallization with oxalic acid from acetone gave the title compound. (Mp 124° C.; M$^+$: 215 and 217; Compound 16).

5.15 C. 1,2,5,6-tetrahydro-3-(4-methoxyethoxy-1,2,5-thiadiazol-3-yl)-1-methylpyridine oxalate To a solution of sodium (120 mg, 5 mmol) in 2-methoxyethanol (10 ml) was added 3-(4-chloro-1,2,5-thiadiazol-3-yl)-1,2,5,6-tetrahydro-1-methylpyridine oxalate (310 mg, 1 mmol). The mixture was stirred at 50° C. for 18 h and evaporated. The residue was dissolved in water and extracted with ethyl acetate. The combined organic phases were dried and evaporated. The title compound was crystallized as the oxalate salt from acetone to yield 270 mg (Mp 152.1° C.; M$^-$: 253; Compound 15).

5.15 D. 3-(4-chloro-1,2,5-thiadiazol-3-yl)-1,2,5,6-tetrahydropyridine hydrochloride To a solution of 3-(4-chloro-1,2,5-thiadiazol-3-yl)-1,2,5,6- tetrahydro-1-methylpyridine (670 mg, 3.1 mmol) in 1,2-dichloroethane (20 ml) was added a solution of 1-chloromethyl-chloroformate (440 mg, 3.1 mmol) in 1,2-dichloroethane at 0° C. The reaction mixture was heated to 40° C. for 2 h and evaporated. The residue was dissolved in methanol and heated to reflux for 1 h. After cooling to room temperature the precipitate was collected by filtration to yield 320 mg (41%) (Mp 224° C.; M$^+$201 and 203; Compound 17).

5.15 E. 3-(4-butoxy-1,2,5-thiadiazol-3-yl)-1,2,5,6 tetrahydropyridine oxalate To a solution of sodium (150 mg, 6.5 mmol) in 1-butanol 15 ml) was added 3-(4-chloro-1,2,5-thiadiazol-3-yl)-1,2,5,6-tetrahydropyridine hydrochloride (240 mg, 1 mmol). The reaction mixture was stirred at 50° C. for 1 h. After evaporation the residue was dissolved in water and extracted with ethyl acetate. The ethyl acetate phase was dried and evaporated to give an oil (200 mg). Crystallization as the oxalate salt from acetone gave the title compound to yield 170 mg (52%) (Mp 173°-174° C.; M$^+$: 239; Compound 18).

5.16 Example 16

5.16 A. 3-(4-chloro-1,2,5-thiadiazol-3-yl)-1-ethylpyridinium iodide

A solution of 3-(4-chloro-1,2,5-thiadiazol-3-yl)pyridine (1.13 g, 5.7 mmol) and ethyl iodide (22.65 g, 17 mmol) in acetone (15 ml) was stirred at 40° C. for 16 h.

The precipitate was collected by filtration giving the title compound to yield 510 mg (26%).

5.16 B.
3-(4-chloro-1,2,5,6-thiadiazol-3-yl)-1-ethyl-1,2,5,6-tetrahydropyridine oxalate To a suspension of sodiumborohydride (170 mg, 4.5 mmol) in ethanol (10 ml) was added 3-(4-chloro-1,2,5-thiadiazol-3-yl)-1-ethylpyridinium iodide (510 mg, 1.5 mmol) at 0° C. The mixture was stirred for 1 h at 0° C. Water was added and the mixture was extracted with ethyl acetate. After drying, the ethyl acetate phase was evaporated and the residue purified by column chromatography (eluent: ethylacetate/methanol (4:1)).Crystallization with oxalic acid from acetone gave the title compound to yield 70 mg (Mp 143° C.; M+: 229 and 231; Compound 19).

5.17 Example 17
5.17 A.
3-(4-ethoxy-1,2,5-thiadiazol-3-yl)-1-ethylpyridinium iodide A solution of 3-(4-ethoxy-12,5-thiadiazol-3-yl)pyridine (0.90 g, 4.3 mmol) and ethyl iodide (2.03 g, 13 mmol) in acetone (4 ml) was stirred at 40° C. for 16 h. The precipitate was collected by filtration giving the title compound to yield 1.34 g (86%).

5.17 B.
3-(4-ethoxy-1,2,5,6-thiadiazol-3-yl)-1-ethyl-1,2,5,6-tetrahydropyridine oxalate To a suspension of sodiumborohydride (410 mg, 10.8 mmol) in ethanol (10 ml) was added 3-(4-ethoxy-1,2,5-thiadiazol-3-yl)-1-ethylpyridinium iodide (1.32 g, 3.6 mmol) at 0° C. The mixture was stirred for 1 h at 0° C. Water was added and the mixture was extracted with ethyl acetate. After drying, the ethyl acetatephase was evaporated and the residue purified by column chromatography (eluent: ethylacetate/methanol (4:1)). Crystallization with oxalic acid from acetone gave a yield of 0.49 g of the title compound (Mp 120°–122° C.; M+: 239; Compound 20).

5.18 Example 18
5.18. A Hydroxyimino-3-pyridylacetonitrile

3-Pyridylacetonitril E (47.2 g, 400 mmol) was dissolved in a solution of sodium hydroxide (16 g, 400 mmol) in methanol (100 ml). Methylnitrite, generated by dropping a solution of concentrated sulphuric acid (12.8 ml) and water (26 ml) to a solution of sodium nitrite (33.2 g, 480 mmol) in water (20 ml) and methanol (20 ml), was bobled through the 3-pyridylacetonitrile E solution at 0° C. The reaction mixture was stirred at 0° C. for 1 hour and the precipitate collected by filtration. The precipitate was washed with a little methanol to give the wanted product in 70% (41.1 g) yield. M+: 147.

5.18 B. Hydroxyimino-3-pyridyl-methylamidoxime

A mixture of hydroxyimino-3-pyridylacetonitrile (41.0 g, 879 mmol), hydroxylamine hydrochloride (21.5 g, 310 mmol) and sodium acetate (50.8 g, 620 mmol) in ethanol (99.9%, 500 ml) was refluxed for 4 hours. After cooling the precipitate was collected by filtration and dried. The precipitate contained the wanted product and sodium acetate (85 g, 168%). M+: 180.

5.18 C. 3-(3-amino-1,.5-oxadiazol-4-yl)pyridine

Crude hydroxyimino-3-pyridylmethylamidoxime (5 g) and phosphorus pentachloride (5 g) was refluxed in dry ether (250 ml) for 6 hours. Water and potassium carbonate to alkaline pH was added and the phases separated. The aqueous phase was extracted with ether and the combined ether phases dried. Evaporation of the ether phases gave the title compound in 850 mg yield. M+: 162.

5.18 D.
3-(3-Amino-1.2.5-oxadiazol-4-yl)-1-methyl-pyridinium iodide

To a solution of 3-(3-amino-1,2,5-oxadiazol-4-yl)pyridine (870 mg, 5.3 mmmol) in acetone (20 ml) was added methyl iodide (990 ul, 16 mmol) and the reaction mixture was stirred over night at room temperature. The title compound precipitated and was collected by filtration (1.1 g, 69%).

5.18 E.
3-(3-Amino-1,2,5-oxadiazol-4-yl)-1,2,5,6-tetrahydro-1-methylpyridine oxalate Sodium borohydride (262 mg, 6.9 mmol) was added to a solution of 3-(3-amino-1,2,5-oxadiazol-4-yl)-1-methylpyridinium iodide (1.05 g, 3.45 mmol) in methanol (80 ml) at 0° C. After 15 min. water (40 ml) was added and the mixture extracted with ether. The ether phase was dried, evaporated and purified by column chromatography (eluent: ethyl-acetate: methanol (2:1)) to give the title compound in 310 mg (50%) yield. Mp. 181°–183° C. M−: 180.

It is to be understood that the invention is not to be limited to the exact details of operation, or to the exact compounds, compositions, methods, procedures, or embodiments shown and described, as obvious modifications and equivalents will be apparent to one skilled in the art, and the invention is therefore to be limited only by the full scope of the appended claims.

We claim:

1. A compound of formula I

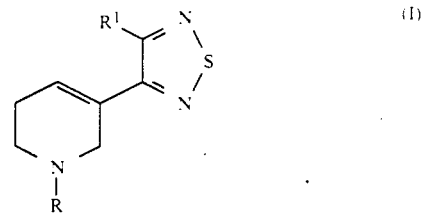

wherein R is H, $C_{1-3}$-alkyl, $C_{3-4}$-cycloalkyl, $C_{2-4}$-alkenyl or $C_{2-4}$-alkynyl and $R^1$ is $C_{1-5}$-alkyl, $C_{2-5}$-alkenyl, $C_{2-5}$-alkynyl, $C_{3-5}$-cycloalkyl, $C_{1-6}$-alkoxy, halogen or amino or a salt thereof with a pharmaceutically-acceptable acid.

2. The compound 3-(4-butoxy-1,2,5-thiadiazole-3-yl)-1,2,5,6-tetrahydro-1-methylpyridine or a salt thereof with a pharmaceutically-acceptable acid.

3. The compound 1,2,5,6-tetrahydro-1-methyl-3-(4-hexyloxy-1,2,5-thiadiazole-3-yl)-pyridine or a salt thereof with a pharmaceutically-acceptable acid.

4. A pharmaceutical composition suitable for use in stimulating the cognitive functions of the forebrain and hippocampus of mammals, including humans, an in treating Alzheimer's disease, comprising an effective amount of a compound of formula I

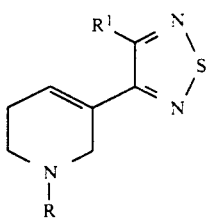

wherein R is H, $C_{1-3}$-alkyl, $C_{3-4}$-cycloalkyl, $C_{2-4}$-alkenyl or $C_{2-4}$-alkynyl and $R^1$ is $C_{1-5}$-alkyl, $C_{2-5}$-alkenyl, $C_{2-5}$-alkynyl, $C_{3-5}$-cycloalkyl, $C_{1-6}$-alkoxy, halogen or amino or a salt thereof with a pharmaceutically-acceptable acid together with a pharmaceutically-acceptable carrier or diluent.

5. The pharmaceutical composition according to claim 4 in the form of an oral dosage unit containing 1-100 mg of the compound of formula I or a salt thereof with a pharmaceutically-acceptable acid.

6. A method of stimulating the cognitive functions of the forebrain and hippocampus and therefore of treating Alzheimer's disease in the subject, in need of such stimulation and/or treatment, comprising the step of administering to said subject an effective amount of a compound of formula I

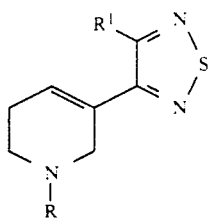

wherein R is H, $C_{1-3}$-alkyl, $C_{3-4}$-cycloalkyl, $C_{2-4}$-alkenyl or $C_{2-4}$-alkynyl and $R^1$ is $C_{1-5}$-alkyl, $C_{2-5}$-alkenyl, $C_{2-5}$-alkynyl, $C_{3-5}$-cycloalkyl, $C_{1-6}$-alkoxy, halogen or amino or a salt thereof with a pharmaceutically-acceptable acid.

7. A method of claim 6 wherein said compound is administered in the form of a pharmaceutical composition together with a pharmaceutically-acceptable carrier or diluent.

8. The method of claim 6 wherein the compound of formula I is selected from the group consisting of 3-(4-butoxy-1,2,5-thiadiazole-3-yl)-1,2,5,6-tetrahydro-1-methylpyridine; and 1,2,5,6-tetrahydro-1-methyl-3-(4-hexyloxy-1,2,5-thiadiazole-3-yl)-pyridine or a salt of the above compounds with a pharmaceutically-acceptable acid.

* * * * *

UNITED STATES PATENT AND TRADEMARK OFFICE
CERTIFICATE OF CORRECTION

PATENT NO. : 5,043,345
DATED : August 27, 1991
INVENTOR(S) : Sauerberg et al.

It is certified that error appears in the above-indentified patent and that said Letters Patent is hereby corrected as shown below:

Col. 4, line 19:   delete "alkoxy, benzyloxy" and insert --alkoxy, phenoxy, benzyloxy--

Col. 10, line 12:   delete "alphaaminoalphaaminoalpha" and insert --alpha-aminoalpha--

Col. 20, line 1:   delete "3-(3-amino 1. .5" and insert --3-(3-amino-1,2,5--

Signed and Sealed this

Twenty-eighth Day of September, 1999

*Attest:*

Q. TODD DICKINSON

*Attesting Officer*    *Acting Commissioner of Patents and Trademarks*